United States Patent
Yu

(10) Patent No.: US 7,008,934 B2
(45) Date of Patent: Mar. 7, 2006

(54) COMPOSITION AND METHOD FOR REDUCING ADVERSE INTERACTIONS BETWEEN PHENOTHIAZINE DERIVATIVES AND PLASMA USING CYCLODEXTRINS

(75) Inventor: Jianwei Yu, Plainsboro, NJ (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 10/183,127

(22) Filed: Jun. 26, 2002

(65) Prior Publication Data

US 2003/0027791 A1    Feb. 6, 2003

Related U.S. Application Data

(60) Provisional application No. 60/301,604, filed on Jun. 28, 2001.

(51) Int. Cl.
 *A61K 31/724* (2006.01)
 *A61K 31/54* (2006.01)

(52) U.S. Cl. .................. 514/58; 514/225.2; 514/225.5; 514/226.2

(58) Field of Classification Search .................. 514/58, 514/225.2, 225.5, 226.2
 See application file for complete search history.

(56) References Cited

OTHER PUBLICATIONS

Uekama, K. et al "Protective effects of cyclodextins . . . " J. Pharm. Dyn. (1981) vol 4, pp 142-144.*

* cited by examiner

*Primary Examiner*—Leigh C. Maier
(74) *Attorney, Agent, or Firm*—Michael C. Mayo

(57) ABSTRACT

Compositions and methods are provided for reducing adverse reactions as a result of parenteral administration of certain phenothiazine derivatives such as promethazine hydrochloride. The active compound may be admixed with an effective amount of one or more cyclodextrin derivatives, and if desired, one or more non-ionic surfactants such as the partial esters of sorbitol and the polyoxyethylene oxides of long chain fatty acids such as the polysorbates.

38 Claims, No Drawings

COMPOSITION AND METHOD FOR REDUCING ADVERSE INTERACTIONS BETWEEN PHENOTHIAZINE DERIVATIVES AND PLASMA USING CYCLODEXTRINS

This application claims priority from provisional application Ser. No. 60/301,604 filed Jun. 28, 2001.

FIELD OF THE INVENTION

The present invention relates to phenothiazine derivatives, and especially to promethazine hydrochloride. In particular, the invention is directed to new compositions containing promethazine hydrochloride and cyclodextrin derivatives, as well as to new methods of minimizing promethazine hydrochloride interactions with plasma proteins by using derivatives of cyclodextrins in aqueous solution formulations. The invention also relates to the use of cyclodextrin derivatives together with certain non-ionic surfactants in aqueous, injectable solutions of phenothiazine derivatives such as promethazine hydrochloride.

BACKGROUND OF THE INVENTION

Promethazine hydrochloride, or 10H-Phenothiazine-10-ethanamine, N,N, α-trimethyl-, monohydrochloride, (±)-, is derived from a class of compounds known as phenothiazines. This compound has been shown to possess antihistaminic, sedative, antimotion-sickness, antiemetic, and anticholinergic effects. An injectable form of the drug has been indicated for the following conditions: 1) amelioration of allergic reactions to blood or plasma; 2) in anaphylaxis as an adjunct to epinephrine and other standard measures after the acute symptoms have been controlled; 3) for other uncomplicated allergic conditions of the immediate type when oral therapy is impossible or contraindicated; 4) active treatment of motion sickness; 5) preoperative, postoperative, and obstetric (during labor) sedation; 6) prevention and control of nausea and vomiting associated with certain types of anesthesia and surgery; 7) as an adjunct to analgesics for the control of postoperative pain; 8) for sedation and relief of apprehension and to produce light sleep from which the patient can be easily aroused; and 9) intravenously in special surgical situations, such as repeated bronchoscopy, ophthalmic surgery, and poor-risk patients, with reduced amounts of meperidine or other narcotic analgesic as an adjunct to anesthesia and analgesia.

U.S. Pat. Nos. 4,246,894; 4,071,620 and 3,981,398 each describe various injectable formulations of promethazine. The parenteral formulation of promethazine hydrochloride, in most cases, is intended for deep intramuscular injection. In occasional use, it can be given through the route of intravenous (i.v.) injection.

When used intravenously, promethazine hydrochloride is generally given in a concentration not greater than about 25 mg/mL and at a rate which generally should not exceed about 25 mg/min. It is preferable to inject the drug through the tubing of an i.v. infusion set that is known to be functioning satisfactorily. However, some incidents of venous thrombosis at the injection site have been encountered.[1] Other clinical case reports involving the use of promethazine HCl have indicated irritation and other serious adverse reactions at the local area of injection, particularly the gangrene at the extremity of the injection site.[2,3] Promethazine hydrochloride has also been reported to raise plasma creatine kinase levels after intramuscular injection, which is an indication of muscle irritation.[4]

In laboratory studies, it has been found that precipitates form immediately when promethazine hydrochloride solution is mixed with plasma in vitro. Without being bound by any particular theory, it is believed that this precipitate formation could be related to the venous thrombosis found at the injection site, as well as the cause of other local adverse reactions involving promethazine hydrochloride injection.

It is therefore an object of the invention to provide new formulations containing additives that can minimize the potential of generating precipitate, thereby reducing the possibility of forming thrombosis, as well as reducing other adverse drug reactions at the local area of, and/or at the distal region to the injection site involving phenothiazine derivatives such as promethazine hydrochloride. The invention should also provide new methods for reducing undesirable side effects, e.g. precipitate formation, pain of injection, associated with the use of parenterally administered, e.g. intramuscularly-administered, phenothiazine derivatives. The formulations should be storage stable and pharmaceutically acceptable.

SUMMARY OF THE INVENTION

In one embodiment the invention provides a composition suitable for parenteral administration containing one or more phenothiazine derivatives. The composition also includes a pharmaceutically acceptable quantity of at least one cyclodextrin derivative which is effective in reducing plasma interactions with the phenothiazine derivatives upon administration to a mammal.

In a further embodiment of the invention, there is a pharmaceutical composition which comprises from about 0.1% to about 70% on a weight/volume (w/v) basis of at least one member selected from the group consisting of phenothiazine derivatives, as well as from about 0.1% to about 90% of at least one member selected from the group consisting of cyclodextrin derivatives.

The invention also provides a method for reducing the formation of precipitates during parenteral administration of a promethazine hydrochloride solution to a mammal, which comprises adding an effective anti-precipitating quantity of at least one cyclodextrin derivative to the solution. An "effective anti-precipitating quantity" would be one which is sufficient to reduce or even eliminate the formation of precipitates, which are now believed to be caused by interactions between promethazine hydrochloride and the plasma proteins which are contained in mammals such as humans.

A further method of the invention is directed to reducing the formation of precipitates during injectable treatment which comprises administering to a mammal (such as a human) a composition containing at least one phenothiazine derivative and at least one cyclodextrin derivative. In addition, the injectable treatment may also include administration of at least one non-ionic surfactant together with the phenothiazine derivative and cyclodextrin derivative.

A method is also provided for reducing the quantity of cyclodextrin derivative necessary to inhibit precipitate formation when a promethazine hydrochloride solution is administered to a patient. By adding an effective amount of at least one non-ionic surfactant, such as a polysorbate, to the solution along with the cyclodextrin derivative, the amount of cyclodextrin which would otherwise be added can then be reduced significantly.

The invention is also directed to an aqueous injectable solution comprising promethazine hydrochloride and an effective precipitate-inhibiting quantity of at least one cyclodextrin derivative, wherein the molar ratio of promethazine hydrochloride to cyclodextrin is within the range of from about 1:0.5 to about 1:4.

Another composition embodiment according to the invention will provide from about 1% to about 15% of promethazine hydrochloride, and from about 5 to about 75% of at least one member selected from the group consisting of cyclodextrin derivatives, wherein the molar ratio of the promethazine hydrochloride to cyclodextrin derivative is within the range of from about 1:1 to about 1:3.

A further formulation of the invention will comprise on a weight/volume (w/v) basis from about 1 to about 15% of promethazine hydrochloride; from about 5 to about 60% of at least one beta-cyclodextrin derivative, and up to about 2% of at least one non-ionic surfactant selected from the group consisting of polysorbates.

In a further aspect of the invention, there is a pharmaceutical composition suitable for parenteral administration, comprising on a weight/volume (w/v) basis from about 1 to about 15% of promethazine hydrochloride; from about 5 to about 60% of gamma-cyclodextrin, wherein the molar ratio of said promethazine hydrochloride to said cyclodextrin is within the range of about 1:1 to about 1:3; and up to about 2% of at least one non-ionic surfactant selected from the group consisting of polysorbates.

The foregoing and other features and advantages of the invention will become more apparent from the detailed description of the preferred embodiments of the invention given below.

DETAILED DESCRIPTION OF THE PREFERRED EMBODIMENTS

The invention is directed to novel compositions and methods of treatment using phenothiazine derivatives. In particular, the invention is directed to preventing, or at least reducing or minimizing, the undesirable side effects associated with injectable treatments of such phenothiazine derivatives as promethazine hydrochloride. The compositions and methods hereinafter described should help to reduce the interaction of the phenothiazine derivatives with plasma proteins, thereby reducing the formation of undesirable precipitates. In turn, incidences of such adverse reactions as irritation and venous thrombosis at the site of parenteral administration should be diminished or eliminated.

Phenothiazine is a widely used anthelmintic (worming agent) in veterinary medicine. It is an organic compound which is highly effective against a broad range of parasites in cattle, horses, poultry, sheep, and swine. A highly toxic drug, it is currently not recommended for human use. Derivatives of phenothiazine are, however, now widely prescribed for humans to control mental disorders such as schizophrenia, paranoia, mania, psychosis resulting from mental deficiency, some forms of senility, hyperactivity in children, and even severe anxiety. The most widely used phenothiazine, chlorpromazine (THORAZINE®) is prescribed for overactive schizophrenics. Another compound, trifluoperazine (STELAZINE®) is used for inhibited and withdrawn schizophrenics. In addition, promethazine hydrochloride has been prescribed for its antihistaminic, sedative, antimotion-sickness, antiemetic, and anticholinergic effects.

As part of the invention, there is provided a novel composition containing one or more active compounds such as phenothiazine derivatives. These would include, without limitation, all FDA-approved compounds such as chlorpromazine, trifluoperazine and promethazine hydrochloride. Of these, promethazine hydrochloride is preferred. Promethazine hydrochloride is identified by the chemical structure:

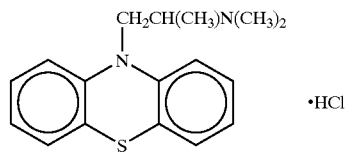

The invention in particular contemplates compositions of phenothiazine derivatives for use in parenteral administration to an animal. The term "parenteral" would therefore encompass all injectables, including without limitation all compositions which are administered intramuscularly, intravenously, intra-arterially, or subcutaneously, for example. The term "animal" would encompass mammals, and in particular would be directed to humans in need of treatment with one or more phenothiazine derivatives such as promethazine hydrochloride.

The compositions herein described may be in any dosage form, but preferably are in liquid form such as in aqueous-based (water) media. Other liquid dosage forms may be contemplated by the skilled artisan provided that they are stable, effective and minimize or eliminate adverse interactions between the active and blood plasma upon administration, as further set forth herein.

A pharmaceutically acceptable quantity of phenothiazine derivative may be utilized, in particular, to yield a dosage amount suitable for an approved indication. As part of the formulation, a preferred concentration will be within the range of about 0.05 to about 95% (w/v) of the phenothiazine derivative(s), e.g. promethazine hydrochloride. Even more preferred is a concentration within the range of about 0.1 to about 70% (w/v), with a range of about 0.1 to about 25% (w/v) being more desirable, and a range of from about 1 to about 15% being even more desirable. Ranges of from about 1 to about 10% may be particularly preferred.

In addition, the compositions will contain at least one cyclodextrin as a constituent thereof. The term "cyclodextrin" or "cyclodextrin derivative" as used herein and unless otherwise specified, shall encompass all cyclodextrins and cyclodextrin compounds, and in particular the hydrophilic derivatives of cyclodextrin. It has now been discovered that the use of cyclodextrin(s) is effective in minimizing or reducing, and in many cases preventing, the formation of precipitates that form as a result of the interaction between the active compound and plasma proteins. Without being bound by any particular theory, it appears that cyclodextrin compound(s) may be highly efficacious in reducing or eliminating the occurrence of undesirable side effects associated with the parenteral, e.g. injectable, administration of such phenothiazine derivatives like promethazine hydrochloride.

Of the cyclodextrin derivatives, the alpha-cyclodextrins, beta-cyclodextrins and gamma-cyclodextrins are preferred for use herein. Even more desirable are the hydrophilic derivatives of beta-cyclodextrin and gamma-cyclodextrin, such as hydroxypropyl beta-cyclodextrin and hydroxypropyl gamma-cyclodextrin, or sulfated beta-cyclodextrin and sulfated beta-gamma-cyclodextrin.

The concentration of the cyclodextrin derivatives in the formulation of the invention will typically be within the range of about 0.1 to about 95% (w/v). A range of about 1 to about 90% is more preferred, and a range of about 5 to about 60% is even more desirable. A molar ratio of active compound to cyclodextrin derivative is preferably within the range of about 1:0.5 to about 1:4. More preferably, the molar ratio of phenothiazine derivative(s), such as promethazine hydrochloride, to the cyclodextrin derivative(s) will be within the range of about 1:1 to about 1:3.

In a further aspect of the invention, an amount of non-ionic surfactant can also be added to the formulation in combination with a cyclodextrin derivative. The addition of a non-ionic surfactant appears to synergistically enhance the precipitate-inhibiting effect of the cyclodextrin. Suitable non-ionic surfactants include one or more of the partial esters of sorbitol and polyoxyethylene oxides of long chain fatty acids known collectively as the polysorbates, the alkylpolyethoxyethanols or the alkarylpolyethoxyethanols. Of the foregoing, polysorbate 80 is preferred. The non-ionic surfactant is typically utilized in an amount less than about 2.0% (w/v). A final concentration of up to about 2.0% (w/v) is preferred, and a concentration within the range of about 0.1% up to about 1.5% is more preferred, with about 0.5% to about 1.5% being more desirable.

An added advantage of the use of at least one non-ionic surfactant is the concomitant reduction in the quantity of cyclodextrin(s) that may be utilized in the composition. It has now been further discovered that the quantity of cyclodextrin(s) in the final formulation may be reduced by at least about 5% (w/v), as compared to an identical composition not containing any non-ionic surfactant. Reductions in the quantity of cyclodextrin(s) of at least about 10% (w/v) and as much as at least about 25% (w/v) or even at least about 33⅓% or even more are also contemplated herein when one or more non-ionic surfactants as heretofore described are also utilized.

The composition of the invention may also contain one or more pH modifiers (buffer agents). These are chemical compounds which are utilized to maintain the composition at a suitable pH. A pH within the range of about 3.5 to about 6.5 is preferred for the composition. Within this range a lower pH is often desirable to help ensure the maximum stability of the preparation. A pH within the range of about 4.0 to about 5.5 is more desirable. Those skilled in the art may discover an optimal pH by analyzing such factors as the heat stability data of the active phenothiazine derivative such as promethazine hydrochloride, in further consideration of the impact of pH on the practical end use of the product.

Other components of the composition of the invention may include one or more anti-oxidants or preservatives to help prevent microbial growth or otherwise inhibit degradation of the final formulation. Any suitable anti-oxidant or preservative stabilizing compound available to the skilled artisan may be utilized in amounts of from about 0.001 to about 1% (w/v) of the composition. For example, sodium metabisulfite or monothioglycerol may be utilized by the skilled artisan as suitable antioxidants and phenol as a proper preservative, for example.

One or more stabilizers may also be utilized in the final formulation. For example, the presence of heavy metal ions is known to accelerate the degradation of an active compound such as promethazine hydrochloride. A chelating agent, such as ethylenediaminetetraacetic acid (EDTA) salts may therefore be useful in stabilizing the composition. When utilized, the stabilizer(s) are typically present in amounts equal to about 0.001 to about 1% (w/v) of the composition.

Since the formulations herein described are preferably aqueous, water will make up the remainder of the compositions in an amount to bring the total of all constituents to about 100% (w/v). Other types of formulations, e.g. oil-based, emulsion, water-in-oil, etc. may also be utilized, provided that they are storage-stable and effective at delivering the active compound.

The formulations of the invention according to the various embodiments may be prepared by dissolving a suitable quantity of the active phenothiazine derivative, e.g. promethazine hydrochloride, in a liquid medium such as water. One or more excipients as heretofore described are then added, or may already be present in the liquid base. Dosage units for parenteral administration may then be prepared using available techniques. As a non-limiting example, dosage preparations for intravenous delivery of promethazine hydrochloride may be administered in a concentration which is less than or equal to about 25 mg/mL or at a rate which is less than or equal to about 25 mg/min. Other concentrations and doses, along with a particular dosing regimen, may then be selected according to the particular indication, typically in consultation with a health professional.

The present invention is further illustrated in more detail by way of the following non-limiting examples.

EXAMPLE 1

An aqueous formulation of promethazine hydrochloride was prepared by dissolving promethazine hydrochloride in a solution of excipients and adjusting the pH with hydrochloric acid/sodium hydroxide. Each mL of the formulation contained 25 mg. of promethazine hydrochloride, 282.0 mg. of hydroxypropyl-beta-cyclodextrin, and a certain amount of a chelating agent, such as 0.1 mg of EDTA disodium and an anti-oxidant, such as 0.25 mg of sodium metabisulfite.

EXAMPLE 2

An aqueous formulation of promethazine hydrochloride was prepared by dissolving promethazine hydrochloride in a solution of excipients and adjusting the pH with hydrochloric acid/sodium hydroxide. Each mL of the formulation contained 50 mg. of promethazine hydrochloride, 564.0 mg. of hydroxypropyl-Beta-cyclodextrin, and a certain amount of a chelating agent, such as 0.1 mg of EDTA disodium and an anti-oxidant, such as 0.25 mg of sodium metabisulfite.

EXAMPLE 3

An aqueous formulation of promethazine hydrochloride was prepared by dissolving promethazine hydrochloride in a solution of excipients and adjusting the pH with hydrochloric acid/sodium hydroxide. Each mL of the formulation contained 25 mg. of promethazine hydrochloride, 212.0 mg. of hydroxypropyl-Beta-cyclodextrin, 7.5 mg. of polysorbate 80, and a certain amount of a chelating agent, such as 0.1 mg of EDTA disodium and an anti-oxidant, such as 0.25 mg of sodium metabisulfite.

EXAMPLE 4

An aqueous formulation of promethazine hydrochloride was prepared by dissolving promethazine hydrochloride in a solution of excipients and adjusting the pH with hydrochloric acid/sodium hydroxide. Each mL of the formulation contained 50 mg. of promethazine hydrochloride, 424.0 mg. of hydroxypropyl-Beta-cyclodextrin, 15.0 mg. of polysorbate 80, and a certain amount of a chelating agent, such as 0.1 mg of EDTA disodium and an anti-oxidant, such as 0.25 mg of sodium metabisulfite.

EXAMPLE 5

An aqueous formulation of promethazine hydrochloride was prepared by dissolving promethazine hydrochloride in a solution of excipients and adjusting the pH with citric acid/sodium citrate. Each mL of the formulation contained 50 mg. of promethazine hydrochloride, 250.0 mg. of hydroxypropyl-gamma-cyclodextrin, 5.0 mg. of polysorbate 80, and a certain amount of a chelating agent, such as 0.1 mg. of EDTA and an anti-oxidant, such as 5 mg. of monothioglycerol.

The overall testing results when the formulation from the above examples were mixed with plasma are summarized in Tables 1 and 2. These results showed minimum formation of precipitate when promethazine hydrochloride solution was mixed with plasma in vitro when a cyclodextrin derivative or a combination of a cyclodextrin derivative and a non-ionic surfactant was added in the promethazine hydrochloride solution. With a composition according to one or more of the embodiments set forth herein, it is expected that a promethazine hydrochloride solution given by the routes of i.v. and i.m. (intramuscular) injection would have fewer incidences of irritation and other adverse reactions at the site of injection.

TABLE 1

Relative Amount of Precipitate Formed When 1 Part of Promethazine Hydrochloride Preparation is Mixed with 10 Parts of Plasma

| Formulations | Upon Addition to Plasma |
| --- | --- |
| Without a Cyclodextrin or surfactant | Precipitate Forms Immediately |
| With a Cyclodextrin | No Precipitate Forms |
| With a Cyclodextrin and a non-ionic surfactant | No Precipitate Forms |

TABLE 2

Relative Amount of Precipitate Formed When 10 Parts of Promethazine Hydrochloride Preparation is Mixed with 1 Part of Plasma

| Formulations | Upon Addition to Plasma |
| --- | --- |
| Without a Cyclodextrin or surfactant | Precipitate Forms Immediately, Redissolves, and Slowly Forms Again |
| With a Cyclodextrin | None to Little Precipitate Forms |
| With a Cyclodextrin and a non-ionic surfactant | No Precipitate Forms |

Although the invention has been described with reference to particular embodiments thereof, it should be appreciated that many changes and modifications can be made without departing from the spirit or scope of the invention. Accordingly, the invention is not to be considered as limited by the foregoing description, but is only limited by the scope of the appended claims.

BIBLIOGRAPHY

1. PHENERGAN® Injection (Wyeth-Ayerst), Physician's Desk Reference, 55th ed., 2001.
2. "Gangrene of the Hand Following Intra-Arterial Injection", Hager D L, Wilson, J N: Anesth. Analg., 47(4): 432–427, 1968.
3. "Accidental Arterial Injection", Webb G A, Lampert, N: Am. J. Obstet. Gynecol., 101(3): 365–371, 1968.
4. "Rise of Activity of Creatine Kinase after Intramuscular Injection of Various Drugs", Kuster J, Medizinische Welt 24/35: (1328–1330), 1973.

The invention claimed is:

1. A pharmaceutical composition suitable for parenteral administration, comprising:
    a) one or more phenothiazine derivatives;
    b) a beta- or gamma- cyclodextrin; and
    c) a polysorbate surfactant, wherein the combination of cyclodextrin and polysorbate synergistically inhibit precipitation caused by interaction of said one or more phenothiazine derivatives and plasma proteins.

2. The composition of claim 1, wherein said phenothiazine derivative is promethazine hydrochloride.

3. The composition of claim 1, wherein said beta- or gamma- cyclodextrin is selected from the group consisting of hydrophilic derivatives of beta-cyclodextrin and gamma-cyclodextrin.

4. The composition of claim 3, wherein said beta- or gamma- cyclodextrin is selected from the group consisting of hydroxypropyl beta-cyclodextrin and gamma-cyclodextrin, and sulfated beta-cyclodextrin and gamma-cyclodextrin.

5. The composition of claim 1, wherein a molar ratio of said phenothiazine derivative to said beta- or gamma-cyclodextrin is within the range of about 1:1 to about 1:4.

6. The composition of claim 7, wherein said molar ratio is within the range of about 1:1 to about 1:3.

7. The composition of claim 1, wherein said polysorbate is polysorbate 80.

8. The composition of claim 1, wherein said polysorbate is present in said composition in an amount equal up to about 2% (w/v) thereof.

9. The composition of claim 1, wherein said polysorbate is present within the range of up to about 1.5%.

10. The composition of claim 1, wherein said composition is suitable for intramuscular, intravenous, intra-arterial, or subcutaneous administered.

11. A pharmaceutical composition suitable for parenteral administration, comprising on a weight/volume (w/v) basis:
    a) from about 0.1 to about 70% of at least one member selected from the group consisting of phenothiazine derivatives;
    b) a beta- or gamma-cyclodextrin; and
    c) at least one non-ionic surfactant in an amount of from about 0.5% up to about 2% of said composition, said non-ionic surfactant being selected from the group consisting of polysorbates, wherein the combination of beta- or gamma- cyclodextrin and at least one non-ionic surfactant synergistically inhibit precipitation caused by interaction of the at least one member and plasma proteins.

12. The composition of claim 11, wherein said at least one member is promethazine hydrochloride.

13. The composition of claim 11, wherein said at least one non-ionic surfactant is polysorbate 80 and said at least one member is promethazine hydrochloride.

14. The composition of claim 11, wherein said at least one non-ionic surfactant is present in said composition in an amount within the range of up to about 1.5% and said phenothiazine derivative is promethazine hydrochloride.

15. The composition of claim 11, further comprising water.

16. The composition of claim 13, further comprising at least one pH modifying agent.

17. The composition of claim 16, wherein said pH modifying agent is present in an amount to maintain said composition within a pH range of about 3.5 to about 6.5.

18. The composition of claim 17, wherein said pH modifying agent is present to maintain said composition within a pH range of about 4.0 to about 5.5.

19. The composition of claim 15, further comprising at least one anti-oxidant.

20. The composition of claim 15, further comprising at least one chelating agent.

21. The composition of claim 20, wherein said chelating agent includes ethylenediaminetetraacidic acid (EDTA).

22. An aqueous injectable solution, comprising promethazine hydrochloride, at least one cyclodextrin selected from the group consisting of beta- and gamma- cyclodextrins, wherein the molar ratio of promethazine hydrochloride to said cyclodextrin is within the range of about 1:0.5 to about 1:4, and at least one non-ionic surfactant selected from the group consisting of polysorbates, wherein the combination of cyclodextrin and at least one non-ionic surfactant synergistically inhibit precipitation caused by interaction of the phenothiazine hydrochloride and plasma proteins contained in the mammal.

23. The aqueous solution of claim 22, wherein said ratio is within the range of about 1:1 to about 1:3.

24. The aqueous solution of claim 22, wherein said at least one non-ionic surfactant is polysorbate 80.

25. A pharmaceutical composition suitable for parenteral administration, comprising on a weight/volume (w/v) basis:
    a) from about 1 to about 15% of promethazine hydrochloride;
    b) from about 5 to about 60% of beta-cyclodextrin, wherein the molar ratio of said promethazine hydrochloride to said beta-cyclodextrin is within the range of about 1:1 to about 1:3; and
    c) from 0.5% to about 2% of at least one non-ionic surfactant selected from the group consisting of polysorbates, wherein the combination of beta-cyclodextrin and at least one non-ionic surfactant synergistically inhibit precipitation caused by interaction of said phenothiazine hydrochloride and plasma proteins.

26. The composition of claim 25, wherein said beta-cyclodextrin is a hydroxypropyl-beta-cyclodextrin.

27. The composition of claim 26, wherein said at least one non-ionic surfactant is polysorbate 80.

28. The composition of claim 27, further comprising at least one chelating agent and at least one antioxidant.

29. The composition of claim 28, further comprising water.

30. A method of reducing the formation of precipitates during parenteral administration of a promethazine hydrochloride solution to a mammal, the method comprising: adding at least one beta- or gamma- cyclodextrin to said solution, and adding at least one non-ionic surfactant to said solution, said at least one non-ionic surfactant being selected from the group consisting of polysorbates, wherein the combination of cyclodextrin and at least one non-ionic surfactant synergistically inhibit precipitation caused by interaction of phenothiazine hydrochloride and plasma proteins.

31. The method of claim 30, wherein said beta- or gamma- cyclodextrin is at least one member selected from the group consisting of the hydroxypropyl beta- and gamma- cyclodextrins or sulfated beta- and gamma-cyclodextrins.

32. The method of claim 30, further comprising adding a pH modifier to said solution so as to yield a pH within the range of about 3.5 to about 6.5.

33. The method of claim 32, further comprising adding at least one anti-oxidant to said solution.

34. A method for reducing the formation of precipitates during injectable treatment which comprises administering to a mammal a composition comprising at least one phenothiazine derivative, at least one cyclodextrin selected from the group consisting of beta- and gamma- cyclodextrins and at least one non-ionic surfactant selected from the group consisting of polysorbates, wherein the combination of cyclodextrin and at least one non-ionic surfactant synergistically inhibit precipitation caused by interaction of the at least one phenothiazine derivative and plasma proteins contained in the mammal.

35. A method for reducing the quantity of beta- or gamma-cyclodextrin necessary to inhibit precipitate formation when a promethazine hydrochloride solution is administered to a patient, the method comprising adding at least one non-ionic surfactant selected from the group consisting of the polysorbates along with said beta- or gamma- cyclodextrin to said solution, wherein the combination of cyclodextrin and at least one non-ionic surfactant synergistically inhibit precipitation caused by interaction of the phenothiazine hydrochloride and plasma proteins contained in the patient.

36. The method of claim 35, wherein said beta- or gamma- cyclodextrin is at least one member selected from the group consisting of hydroxypropyl beta- and gamma-cyclodextrins or sulfated beta- and gamma- cyclodextrins.

37. The method of claim 36, wherein said beta- or gamma- cyclodextrin is hydroxypropyl beta-cyclodextrin.

38. The method of claim 35, wherein said beta- or gamma- cyclodextrin is hydroxypropyl beta-cyclodextrin and said at least one non-ionic surfactant is polysorbate 80.

* * * * *

UNITED STATES PATENT AND TRADEMARK OFFICE
CERTIFICATE OF CORRECTION

PATENT NO. : 7,008,934 B2 Page 1 of 1
APPLICATION NO. : 10/183127
DATED : March 7, 2006
INVENTOR(S) : Jianwei Yu It is certified that error appears in the above-identified patent and that said Letters Patent is hereby corrected as shown below:

In the claims:

In claim 6, Col. 8, line 28, change "claim 7" to --claim 5--.

Signed and Sealed this

Thirteenth Day of March, 2007

JON W. DUDAS
*Director of the United States Patent and Trademark Office*